United States Patent
Trzaska et al.

(10) Patent No.: US 9,604,971 B2
(45) Date of Patent: Mar. 28, 2017

(54) CO-CRYSTAL OF THE PAR-1 RECEPTOR ANTAGONISTS VORAPAXAR AND ASPIRIN

(71) Applicant: ARALEZ PHARMACEUTICALS TRADING DAC, Dublin (IE)

(72) Inventors: Scott Trzaska, Raritan, NJ (US); Alicia V. Duran-Capece, South Plainfield, NJ (US); Matthew Lamm, Morristown, NJ (US)

(73) Assignee: ARALEZ PHARMACEUTICALS TRADING DAC, Dublin (IE)

( * ) Notice: Subject to any disclaimer, the term of this patent is extended or adjusted under 35 U.S.C. 154(b) by 0 days.

(21) Appl. No.: 14/905,193

(22) PCT Filed: Jul. 17, 2014

(86) PCT No.: PCT/US2014/046929
§ 371 (c)(1),
(2) Date: Jan. 14, 2016

(87) PCT Pub. No.: WO2015/013083
PCT Pub. Date: Jan. 29, 2015

(65) Prior Publication Data
US 2016/0159779 A1  Jun. 9, 2016

Related U.S. Application Data

(60) Provisional application No. 61/856,772, filed on Jul. 22, 2013.

(51) Int. Cl.
*C07D 405/06* (2006.01)
*A61K 31/443* (2006.01)
*A61K 31/616* (2006.01)
*C07C 69/157* (2006.01)

(52) U.S. Cl.
CPC .......... *C07D 405/06* (2013.01); *A61K 31/443* (2013.01); *A61K 31/616* (2013.01); *C07C 69/157* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,645,987 B2 | 11/2003 | Chackalamannil et al. |
| 6,894,065 B2 | 5/2005 | Chackalamannil et al. |
| 7,235,567 B2 | 6/2007 | Wu |
| 7,304,078 B2 | 12/2007 | Chackalamannil et al. |
| 7,488,742 B2 | 2/2009 | Chackalamannil et al. |
| 2007/0202140 A1 | 8/2007 | Veltri et al. |
| 2007/0232635 A1 | 10/2007 | Chelliah et al. |
| 2007/0270439 A1 | 11/2007 | Chackalamannil et al. |
| 2010/0311701 A1 | 12/2010 | Almarsson et al. |
| 2012/0184504 A1 | 7/2012 | Strony et al. |

FOREIGN PATENT DOCUMENTS

WO    WO2013134012 A1    9/2013

OTHER PUBLICATIONS

Database CAPLUS in STN, Acc. No. 2012:1260711, Scirica et al., Lancet (2012), 380(9850), pp. 1317-1324 (abstract).*
Database CAPLUS in STN, Acc. No. 2012:1110156, Almarsson et al., Pharmaceutical Patent Analyst (2012), 1(3), pp. 313-327 (abstract).*
International Search Report and Written Opinion for PCT/US2014/046929 mailed Oct. 8, 2014; 7 pages.

* cited by examiner

*Primary Examiner* — Brian J Davis
(74) *Attorney, Agent, or Firm* — Parker Highlander PLLC (57) ABSTRACT

This invention relates to a co-crystal of vorapaxar and aspirin. The inventive co-crystal antagonizes the PAR-1 receptor. This invention also provides for pharmaceutical compositions comprising the inventive co-crystal as well as potentially to methods for the treatment, amelioration or prevention of conditions that could be treated by antagonizing the PAR-1 receptor.

13 Claims, 9 Drawing Sheets

CO-CRYSTAL OF THE PAR-1 RECEPTOR ANTAGONISTS VORAPAXAR AND ASPIRIN

CROSS REFERENCE TO RELATED APPLICATIONS

This application is a U.S. National Phase application under 35 U.S.C. §371 of PCT Application No. PCT/US2014/046929 filed Jul. 17, 2014, which claims priority from U.S. Provisional Application Ser. No. 61/856,772, filed Jul. 22, 2013.

FIELD OF THE INVENTION

The present invention relates to a co-crystal of the protease activated receptor-1 (PAR-1) antagonist (or thrombin receptor antagonist) [(1R,3aR,4R,6R,8aR,9S,9aS)-9-[(E-2-[5-3-fluorophenyl]-2-pyridinyl)ethenyl]-dodecahydro-1-methyl-3-oxonaphtho[2,3-c]furan-6-yl]carbamate or vorapaxar and the cardiovascular agent acetylsalicylic acid or aspirin ("inventive co-crystal") The inventive co-crystal is a co-crystal of two compounds that the art recognizes as having pharmaceutical activity, instead of the more typical situation where the co-crystal former is an inert spectator. The inventive co-crystal may be expected to be useful in treating disease states such as acute coronary syndrome ("ACS") (unstable angina, non-ST-segment elevation ("NSTE"), myocardial infarction ("MI"), and ST segment-elevation myocardial infarction ("STEW"), secondary prevention of myocardial infarction or thrombotic stroke ("secondary prevention") or peripheral artery diseases ("PAD"), which is also known in the art as peripheral vascular disease. The present invention also relates to pharmaceutical compositions comprising the inventive co-crystal as well as processes for their preparation.

BACKGROUND OF THE INVENTION

Co-crystals are solid-state, crystalline materials that are composed of two or more molecules in the same crystal lattice. Co-crystals are distinguishable from other pharmaceutical solid-state forms, such as polymorphs or salts, as these other solid-state forms only contain the active pharmaceutical ingredient ("API") within the crystal lattice, whereas co-crystals are composed of an API with a guest compound in the crystal lattice. Two or more of the molecules in a co-crystal are, neutral, interact via nonionic interactions, and are solids at room temperature when isolated as individual components Typically, co-crystals are prepared by crystallizing an API with a guest compound. Guest compounds are compounds that possess the ability to form complementary non-covalent interactions with the API. General classes of guest compounds include compounds having alcohol, ketone, ester and/or carboxylic acid functionalities. Co-crystals of different APIs are known in the art. See, e.g., U.S. Pat. No. 8,163,790 B2; U.S. Pat. No. 8,097,593; U.S. Pat. Nos. 8,003,700 and 8,039,475, Co-crystals form in situations where favorable interactions between the individual components exist and one might expect to see improved physical properties, such as solubility, hygroscopicity and compaction behavior. Sekhon, *ARS Pharm.*, 50(3), pp 99-117 (2009).

Thrombin is known to have a variety of activities in different cell types. PAR-1 receptors are known to be present in such cell types as human platelets, vascular smooth muscle cells, endothelial cells and fibroblasts. It is expected that PAR-1 receptor antagonists will be useful in the treatment of thrombotic, inflammatory, atherosclerotic and fibroproliferative disorders, as well as other disorders in which thrombin and its receptor play a pathological role.

Substituted bi- and tricyclic thrombin receptors antagonists are known in the art and the art suggests that these receptor antagonists will treat thrombin receptor mediated disorders such as thrombosis, atherosclerosis, restenosis, hypertension, angina pectoris, angiogenesis related disorders, arrhythmia, a cardiovascular or circulatory disease or condition, heart failure, ACS, MI, glomerulonephritis, thrombotic stroke, thromboembolytic stroke, PAL), deep vein thrombosis, venous thromboembolism, a cardiovascular disease associated with hormone replacement therapy, disseminated intravascular coagulation syndrome and cerebral infarction, as well as $CB_2$ receptor mediated disorders. See, e.g., U.S. Pat. No. 7,304,048 or U.S. Pat. No. 6,645,987, U.S. Pat. No. 6,645,987 and U.S. Pat. No. 6,894,065 disclose PAR-1 receptor antagonists of the structure:

where $R^{10}$ may be groups such as H, alkyl, haloalkyl, hydroxyl, etc, and $R^{22}$ may be groups such as H, optionally substituted alkyl, hydroxyl, etc. Other known substituted thrombin receptor antagonists are disclosed in U.S. Pat. No. 6,063,847, U.S. Pat. No. 6,326,380, U.S. Pat. No. 7,037,920, U.S. Pat. No. 7,488,742, U.S. Pat. No. 7,713,999, U.S. Pat. No. 7,442,712, U.S. Pat. No. 7,488,752, U.S. Pat. Nos. 7,776,889, 7,888,369, U.S. Pat. No. 8,003,803, U.S. Pat. No. 8,022,088, US 2008/0090830, and Chackalamannil et al., *J. Med. Chem.*, 49, p. 5389 (2006).

Figure 1:
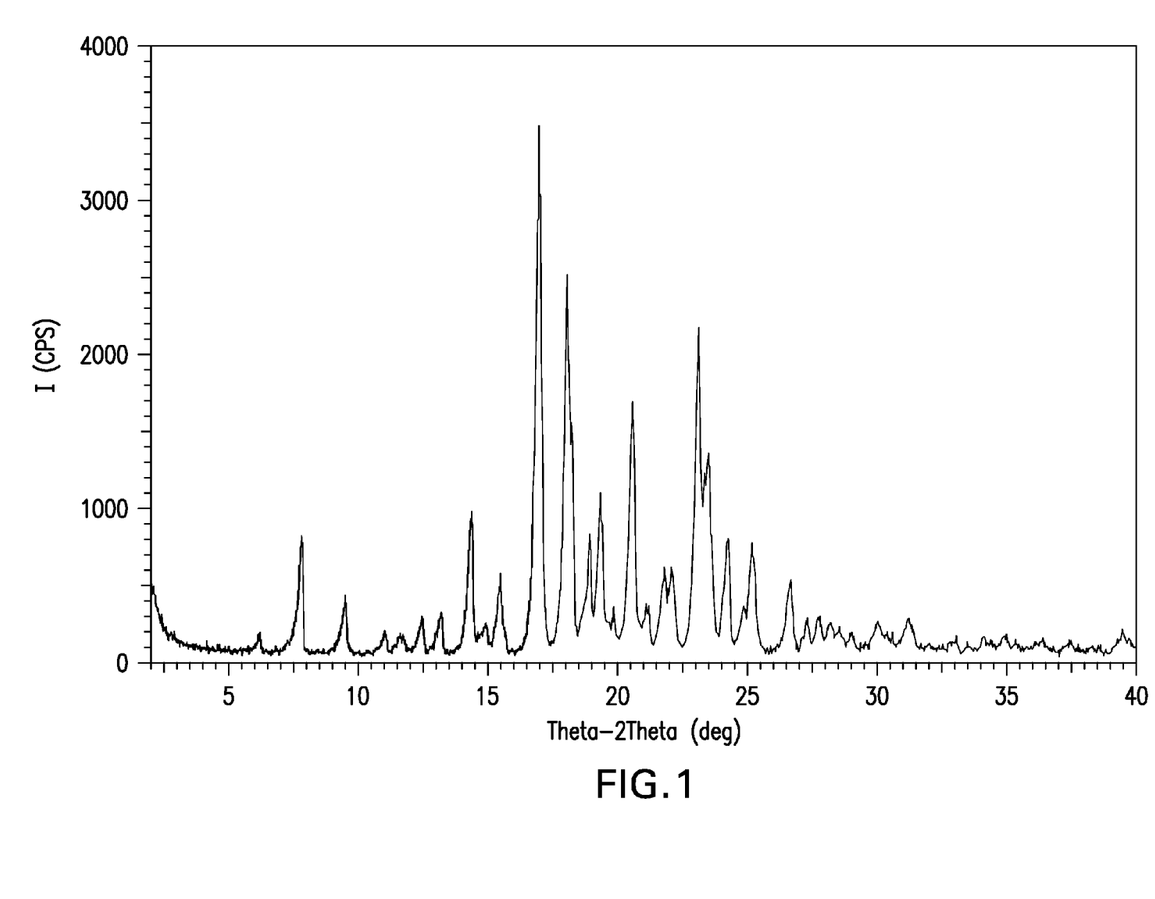
FIG. 1 is a graph of a PXRD pattern of the co-crystal of vorapaxar and aspirin having a molar ratio of vorapaxar to aspirin of 1:1 in the unit cell, generated using a Kratos XRD 6000 diffractometer. The graph plots the intensity of the peaks as defined by counts per second versus the diffraction angle 2 theta in degrees.
Figure 2:
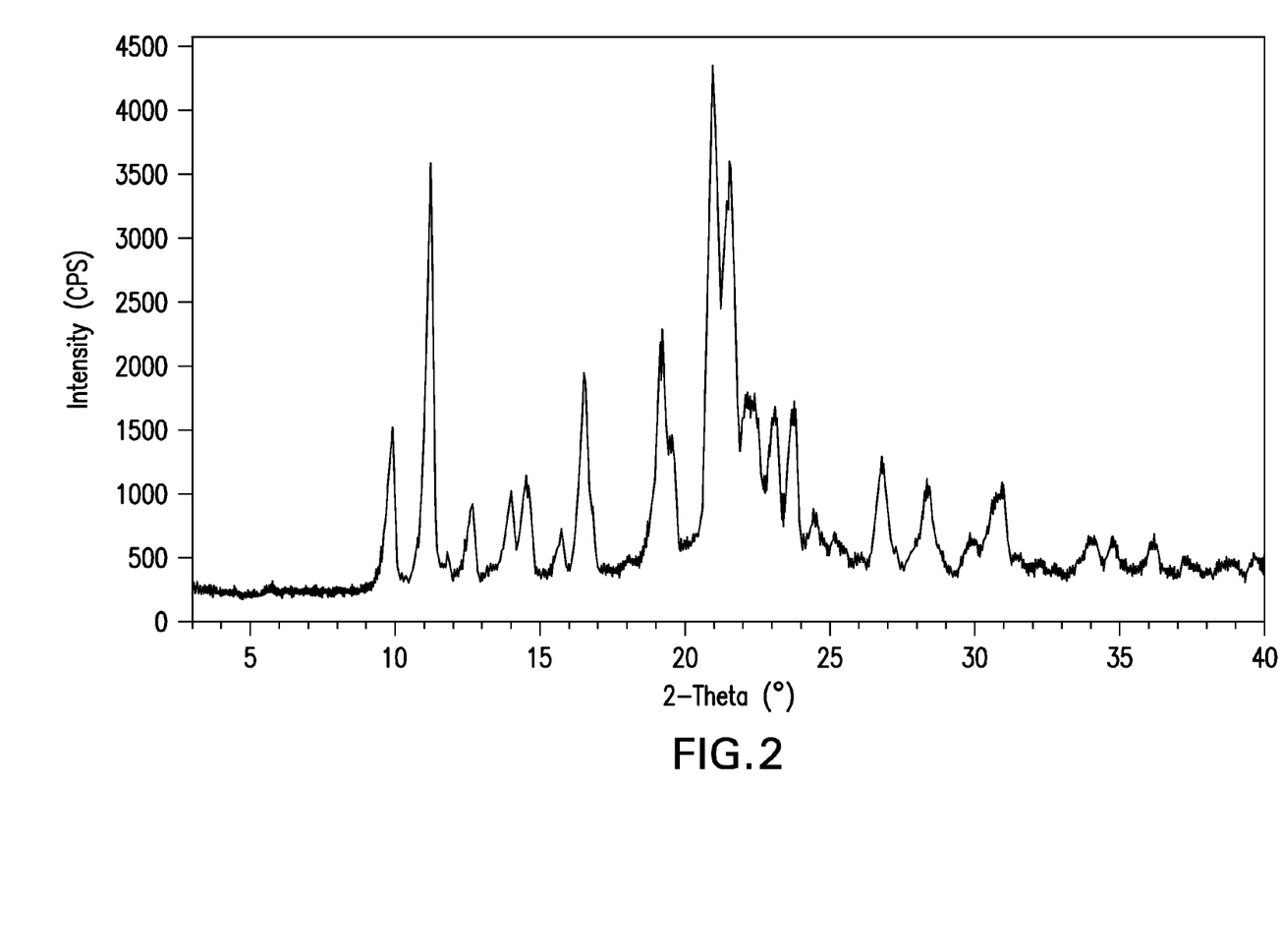
FIG. 2 is a graph of a PXRD pattern of Form 1 of vorapaxar bisulfate taken from U.S. Pat. No. 7,253,567. The PXRD pattern was crystallized from acetonitrile and generated using a Rigaku MiniFlex diffractometer. The graph plots the intensity of the peaks as defined by counts per second versus the diffraction angle 2 theta in degrees.

A PAR-1 receptor antagonist that exhibits good thrombin receptor antagonist activity (potency) and selectivity is vorapaxar (Merck & Co., Inc.), which has the following structure:

This compound has undergone clinical trials (TRA-CER and TRA 2°P) and is disclosed in U.S. Pat. No. 7,304,048. U.S. Pat. No. 7,235,567 discloses the bisulfate salt of vorapaxar and indicates that this salt has at least two crystalline polymorphic forms; viz., Form 1 and Form 2. FIG. 1 is a powder x-ray diffraction (PXRD) pattern of Form 1 of the bisulfate salt of vorapaxar and FIG. 2 is a PXRD of Form 2. U.S. Pat. No. 7,235,567 indicates that Form 2 was found to be unstable and reverted over time to the crystalline structure of Form 1. An advantage of the inventive co-crystal is that they do not exist in other polymorphic forms or form solvates.

U.S. Patent Applications US 2008/0026050 A1; US 2008/0031943 A1; and US 2008/0152712 A1 disclose capsule formulations, tablet formulations and lyophilized formulations (respectively) of vorapaxar or a pharmaceutically acceptable salt thereof as well methods of treating various conditions affected by antagonizing the PAR-1 receptor by administering same to a patient. U.S. Pat. No. 7,304,048 and U.S. Pat. No. 7,235,567 describe inter alia pharmaceutical combinations of vorapaxar and aspirin. Other pharmaceutical combinations of vorapaxar and other cardiovascular agents are described in US 2007/023874 A1.

There is a need to develop pharmaceutical formulations comprising vorapaxar as an active agent wherein vorapaxar exhibits polymorphic simplicity (i.e., does not form other polymorphic forms or solvates). This and other objectives will become evident from the following description.

SUMMARY OF THE INVENTION

In its many embodiments, the present invention is directed to a co-crystal of vorapaxar and aspirin, pharmaceutical compositions comprising the same and, potentially, to a method of treating, preventing, inhibiting or ameliorating one or more disease states associated with antagonizing both the PAR-1 receptor by administering an effective amount of the inventive co-crystal to a patient or mammal in need thereof. The present invention also provides a process for preparing the inventive co-crystal of vorapaxar and aspirin.

Another aspect of the present invention is pharmaceutical compositions comprising a therapeutically effective amount of a co-crystal of vorapaxar and aspirin and a pharmaceutically acceptable carrier.

Another aspect of the present invention is pharmaceutical compositions comprising a therapeutically effective amount of a co-crystal of vorapaxar and aspirin, a second therapeutic agent (e.g., aspirin) and a pharmaceutically acceptable carrier.

The compounds of the present invention could be useful in the treatment, amelioration or prevention of one or more conditions associated with antagonizing the PAR-1 receptor by administering a therapeutically effective amount of a co-crystal of vorapaxar and aspirin of to a mammal in need of such treatment. Conditions that could be treated or prevented by antagonizing the PAR-1 receptor include ACS, secondary prevention, PAD, thrombosis, atherosclerosis, restenosis, hypertension, angina pectoris, arrhythmia, heat failure, MI, glomerulonephritis, thrombotic stroke, thromboembolic stroke, deep vein thrombosis, venous embolism a cardiovascular disease associated with hormone replacement therapy, renal ischemia, cerebral stroke, cerebral ischemia, cerebral infarction, migraine, or renal vascular homeostasis. Other conditions that could be treated by antagonizing the PAR-1 receptor are the reduction of atherothrombotic events in patients with a history of MI and reducing the rate of a combined endpoint of cardiovascular death, MI, stroke and urgent coronary revascularization.

Another embodiment of the present invention is the use of a co-crystal of vorapaxar and aspirin for the manufacture of a medicament for the treatment, amelioration or prevention of one or more conditions associated with antagonizing the PAR-1 receptor.

DETAILED INSCRIPTION

In an embodiment, the present invention provides a co-crystal of vorapaxar and aspirin.

Another embodiment of the present invention is a co-crystal of vorapaxar and aspirin having a molar ratio of vorapaxar to aspirin of 1:1 in the unit cell.

Another embodiment of the present invention is a co-crystal of vorapaxar and aspirin having characteristic peak locations at degrees 2 theta of 16.9, 18.1, 20.5, and 23.0 measured by X-ray powder diffraction.

Another embodiment of the present invent on is a co-crystal of vorapaxar and aspirin having characteristic peak locations at degrees 2 theta of 14.2, 16.9, 18.1, 19.3, 20.5, 23.0, 23.4, and 24.1 measured by X-ray powder diffraction.

Another embodiment of the present invention is a co-crystal of vorapaxar and aspirin having characteristic peak locations at degrees 2 theta of 7.7, 14.2, 16.9, 18.1, 18.9, 19.3, 20.5, 21.9, 23.0, 23.4, 24.1, and 25.0 measured by X-ray powder diffraction.

Another embodiment of the present invention is a co-crystal of vorapaxar and aspirin having substantially the same x-ray diffraction pattern as FIG. 1.

Another embodiment of the present invention is a co-crystal of vorapaxar and aspirin having an endothermic peak at about 148.7° C., measured by differential scanning calorimetry.

Another embodiment of the present invention is a co-crystal of vorapaxar and aspirin having an endothermic peak at about 148.7, measured by differential scanning calorimetry and having characteristic peak locations at degrees 2 theta of 14.2, 16.9, 18.1, 19.3, 20.5, 23.0, 23.4, and 24.1 measured by X-ray powder diffraction.

Another embodiment of the present invention is a co-crystal of vorapaxar and aspirin having an endothermic peak at about 148.7° C., measured by differential scanning calorimetry and having characteristic peak locations at degrees 2 theta of 14.2, 16.9, 18.1, 19.3, 20.5, 23.0, 23.4, and 24.1 measured by X-ray powder diffraction.

Another embodiment of the present invention is a co-crystal of vorapaxar and aspirin having an endothermic peak at about 148.7° C., measured by differential scanning calorimetry and having characteristic peak locations at degrees 2 theta of 7.7, 14.2, 16.9, 18.1, 18.9, 19.3, 20.5, 21.9, 23.0, 23.4, 24.1, and 25.0 measured by X-ray powder diffraction.

As used throughout the specification, the following terms, unless otherwise indicated, shall be understood to have the following meanings:

"Patient" includes both human and other animals.

"Mammal" includes humans and other mammalian animals.

"Co-crystal" means solid-state, crystalline material that is composed of two or more molecules in the same crystal lattice which are solids as individual components at room temperature "Polymorph" means a crystalline form of a substance that is distinct from another crystalline form but that shares the same chemical formula.

"Excipient" means an essentially inert substance used as a diluent or to give form or consistency to a formulation.

"Effective" or "therapeutically effective" is meant to describe a compound or a composition of the present invention effective in antagonism of thrombin receptors and thus producing the desired therapeutic, ameliorative, inhibitory or preventative effect. "Effective amount" or "therapeutically effective amount" is meant to describe an amount of compound or a composition of the present invention effective in antagonism of thrombin receptors and thus producing the desired therapeutic, ameliorative, inhibitory or preventative effect. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" are used herein to refer to administering a compound before the onset of clinical symptoms.

The term "pharmaceutical composition" is intended to encompass both the bulk composition and individual dosage units comprised of more than one (e.g., two) pharmaceutically active agents such as, for example, the inventive co-crystal and an additional agent selected from the lists of the additional agents described herein, along with any pharmaceutically acceptable carrier. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Sample Preparation

Samples of a co-crystal of vorapaxar and aspirin were prepared as described in example 1, No particle size reduction or milling was performed and the material was analyzed as it was isolated.

Powder X-Ray Diffraction

The PXRD diffraction data was collected using a Kratos XRD 6000 diffractometer with a scintillation counter detector. The sample was prepared by lightly packing the material into a glass sample holder followed by gentle smoothing to produce a flat sample surface. Copper (Kα) radiation generated at 40.0 kV and 35.0 mA was used. The slit dimensions were fixed at 0.50 degrees for divergence, 0.50 degrees for scattering, and 0.15 mm for receiving. The sample was analyzed from 2 to 40 degrees 2 Theta with a step size of 0.02 degrees over step durations of 0.6 seconds. Data analysis was conducted using Basic Process software version 2.6 supplied by Shimadzu. The data was smoothed using the automatic smoothing process in the software.

Using the methods and equipment described above, the co-crystal of vorapaxar and aspirin (molar ratio 1:1) was subjected to PXRD analysis. A PXRD pattern was generated and is displayed in FIG. 1. The intensity of the peaks (y-axis is in counts per second) is plotted versus the 2θ angle (x-axis is in degrees 2θ). In addition, the data were plotted with detector counts normalized for the collection time per step versus the 2θ angle. Peak locations (on the 2θ X-axis) consistent with these profiles are displayed in Table 1. The locations of these PXRD peaks are characteristic of the co-crystal of vorapaxar and aspirin.

TABLE 1

PXRD Peak Positions for the Co-crystal of Vorapaxar and Asprin
2 Theta (Degrees)

6.2
7.7
9.4
11.0
12.4
13.0
14.2
14.7
15.4
16.9
18.1
18.9
19.3
19.7
20.5
21.7
21.9
23.0
23.4
24.1
25.0
26.4
27.1

TABLE 1-continued

PXRD Peak Positions for the Co-crystal of Vorapaxar and Asprin
2 Theta (Degrees)

27.6
28.0
29.8

Starting with the PXRD peak locations of the co-crystal of vorapaxar and aspirin (molar ratio 1:1) as displayed in Table 1, the most characteristic peak locations can be selected and grouped by relative intensity to conveniently distinguish this crystalline structure from others. This selection of unique peaks is displayed in Table 2. Thus, the crystalline structure of the inventive co-crystal may be identified by the Peak Location Group No. 1, consisting of four characteristic PXRD peak locations. In another embodiment, the crystalline structure of the inventive co-crystal may be identified by the Peak Location Group No. 2, consisting of the four characteristic PXRD peak locations of Group No. 1 and an additional four peak locations. Still in another embodiment, the crystalline structure of the inventive co-crystal may be identified by the Peak Location Group No. 3, consisting of the eight characteristic PXRD peak locations of Group No. 2 and an additional four peak locations.

TABLE 2

Characteristic PXRD Peak Locations for
the co-crystal of Vorapaxar and Aspirin

| Peak Location Group No. | Peak Location (degrees 2) |
|---|---|
| 1 | 16.9 |
|   | 18.1 |
|   | 23.0 |
|   | 20.5 |
| 2 | 16.9 |
|   | 18.1 |
|   | 23.0 |
|   | 20.5 |
|   | 23.4 |
|   | 19.3 |
|   | 14.2 |
|   | 24.1 |
| 3 | 16.9 |
|   | 18.1 |
|   | 23.0 |
|   | 20.5 |
|   | 23.4 |
|   | 19.3 |
|   | 14.2 |
|   | 24.1 |
|   | 7.7 |
|   | 18.9 |
|   | 25.0 |
|   | 21.9 |

Those skilled in the art recognize that the measurements of the PXRD peak locations for a given crystalline form of the same compound will vary within a margin of error.

Figure 3:
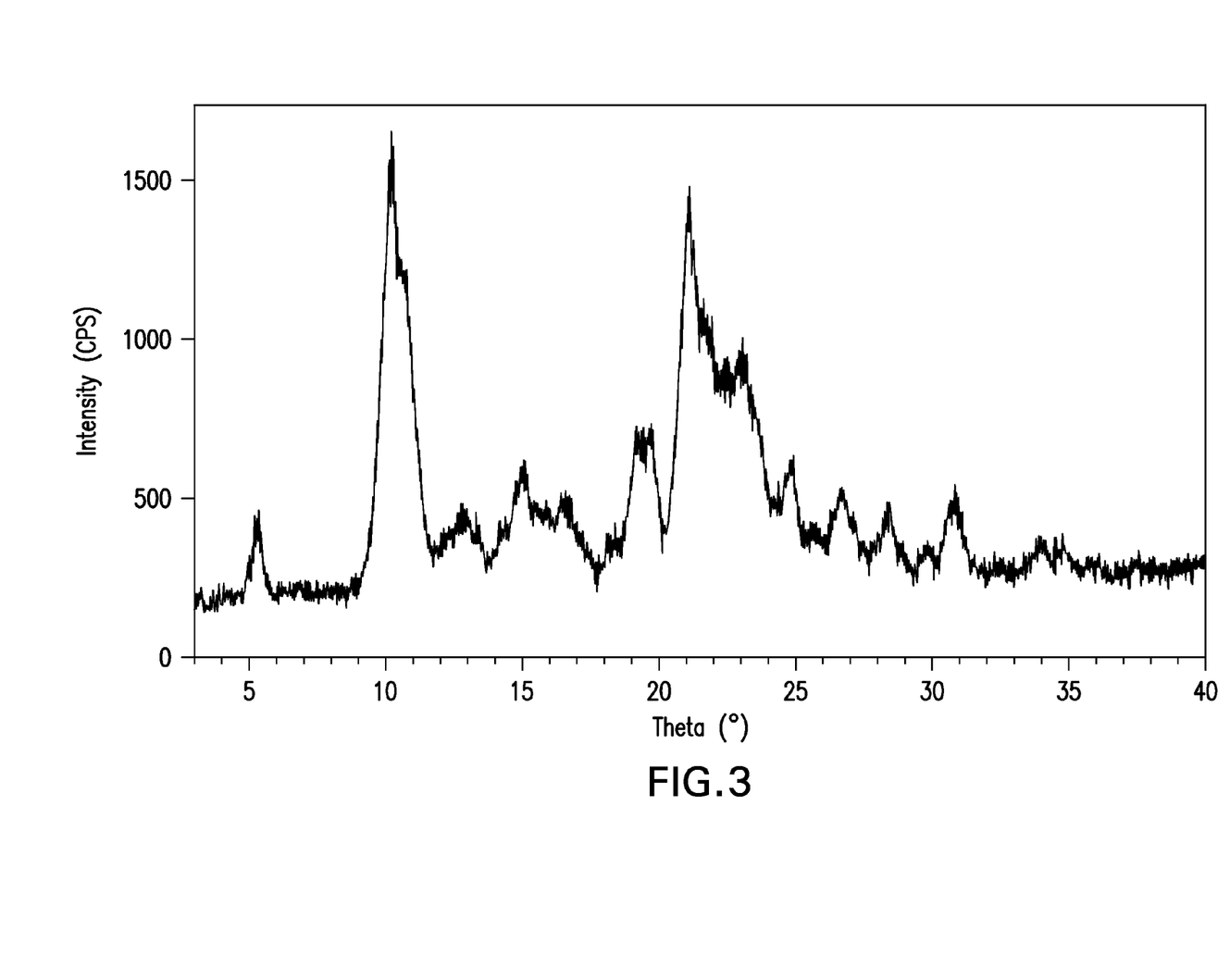
FIG. 3 is a graph of a PXRD pattern of Form 2 of vorapaxar bisulfate taken from U.S. Pat. No. 7,253,567. The PXRD pattern was crystallized from acetonitrile, generated using a Rigaku MiniFlex diffractometer. The graph plots the intensity of the peaks as defined by counts per second versus the diffraction angle 2 theta in degrees.

A comparison of the PXRD pattern of FIG. 1 with the PXRD pattern of FIGS. 2 and 3 supports the conclusion that the co-crystal of vorapaxar and aspirin is not polymorphic Form 1 or Form 2 of vorapaxar bisulfate.

Differential Scanning Calorimry

The DSC instrument used to test the co-crystal sample was a TA Instruments, model Q100 (New Castle, Del.). Approximately 1 to 5 milligrams of sample were sealed in hermetic aluminum pans and two pinholes were punched into the lid of each sample pan. Analyses were conducted under a nitrogen purge of 50 mL per minute with a heating rate of 10° C. per minute. The instrument was calibrated with high purity indium. The accuracy of the measured sample temperature with this method is within about +/−1° C., and the heat of fusion can be measured within a relative error of about +/−5%. The heat flow, which was normalized by a sample weight, was plotted versus the measured sample temperature. The data were reported in units of watts/gram ("W/g"). The plot was made with the endothermic peaks pointing down.

Figure 4:
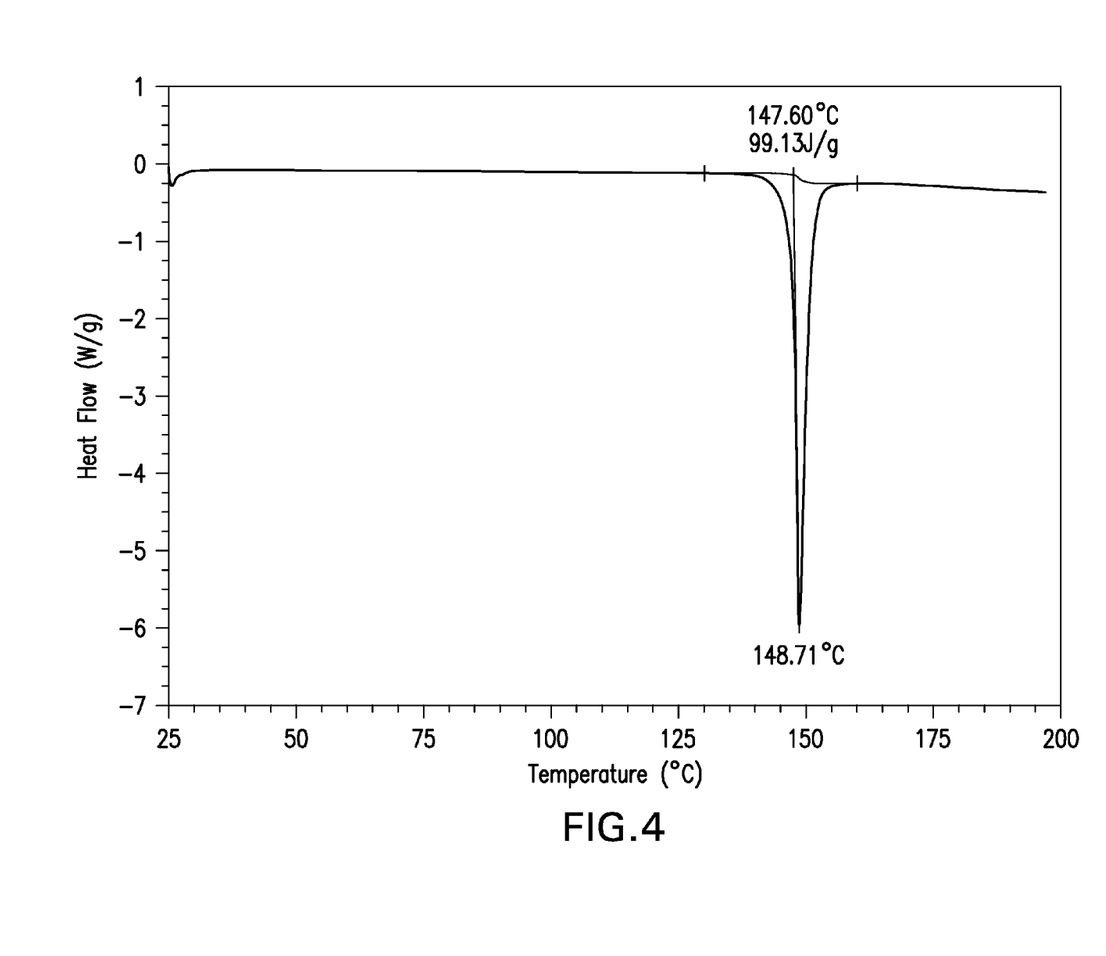
FIG. 4 is a graph of a differential scanning calofimetry ("DSC") thermogram of the co-crystal of vorapaxar and aspirin having a molar ratio of vorapaxar to aspirin of 1:1 in the unit cell. The graph plots the normalized heat flow in units of Watts/gram (W/g) versus the measured sample temperature (° C.) with exotherms up.

FIG. 4 depicts a DSC profile for the co-crystal of vorapaxar and aspirin (molar ratio 1:1). FIG. 3 shows a single sharp melting endotherm with an extrapolated onset temperature of 147.6° C. and a peak temperature of 148.7° C., which is indicative of a single crystalline species. The heat of fusion is 99.1 kg. The combination of melt temperature and heat of fusion is used to distinguish this co-crystal from other crystalline forms.

Thermogravimetric Analysis

The instrument used to perform a TGA on the co-crystal sample was a TA Instruments, model Q50 (New Castle, Del.). Approximately 5 to 15 milligrams of the co-crystal of vorapaxar and aspirin were placed in a platinum pan and heated at 10° C. per minute from room temperature to 300° C. under a nitrogen purge with a flow rate of 60 mL/min.

Figure 5:
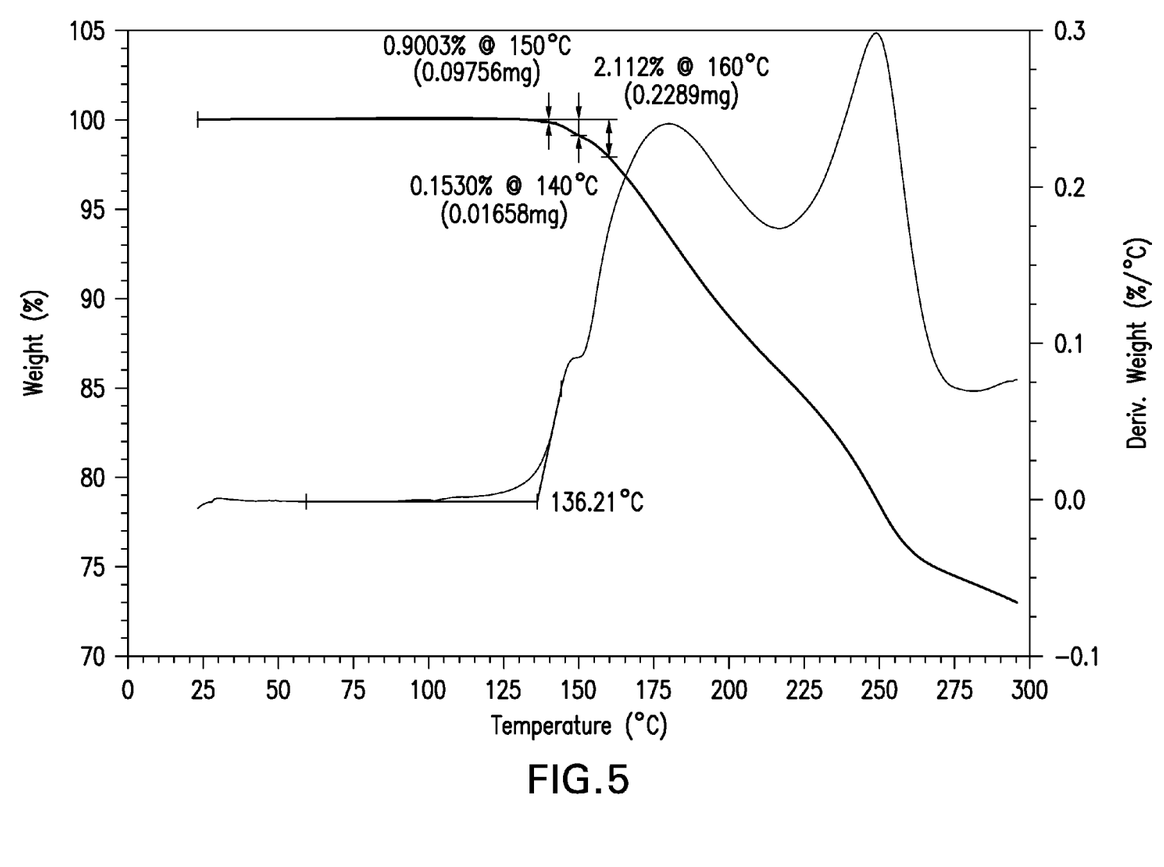
FIG. 5 is a graph of a thermal gravimetric analysis (TGA) the co-crystal of vorapaxar and aspirin having a molar ratio of vorapaxar to aspirin of 1:1 in the unit cell. The graph plots weight (percentage) against temperature (° C.).

FIG. 5 shows the TGA data for the co-crystal of vorapaxar and aspirin (molar ratio 1:1). The data do not show any significant thermal decomposition or weight loss attributable to the presence of solvent or other volatiles is occurring below the melting point of the co-crystal.

Dynamic Vapor Sorption

Figure 6:
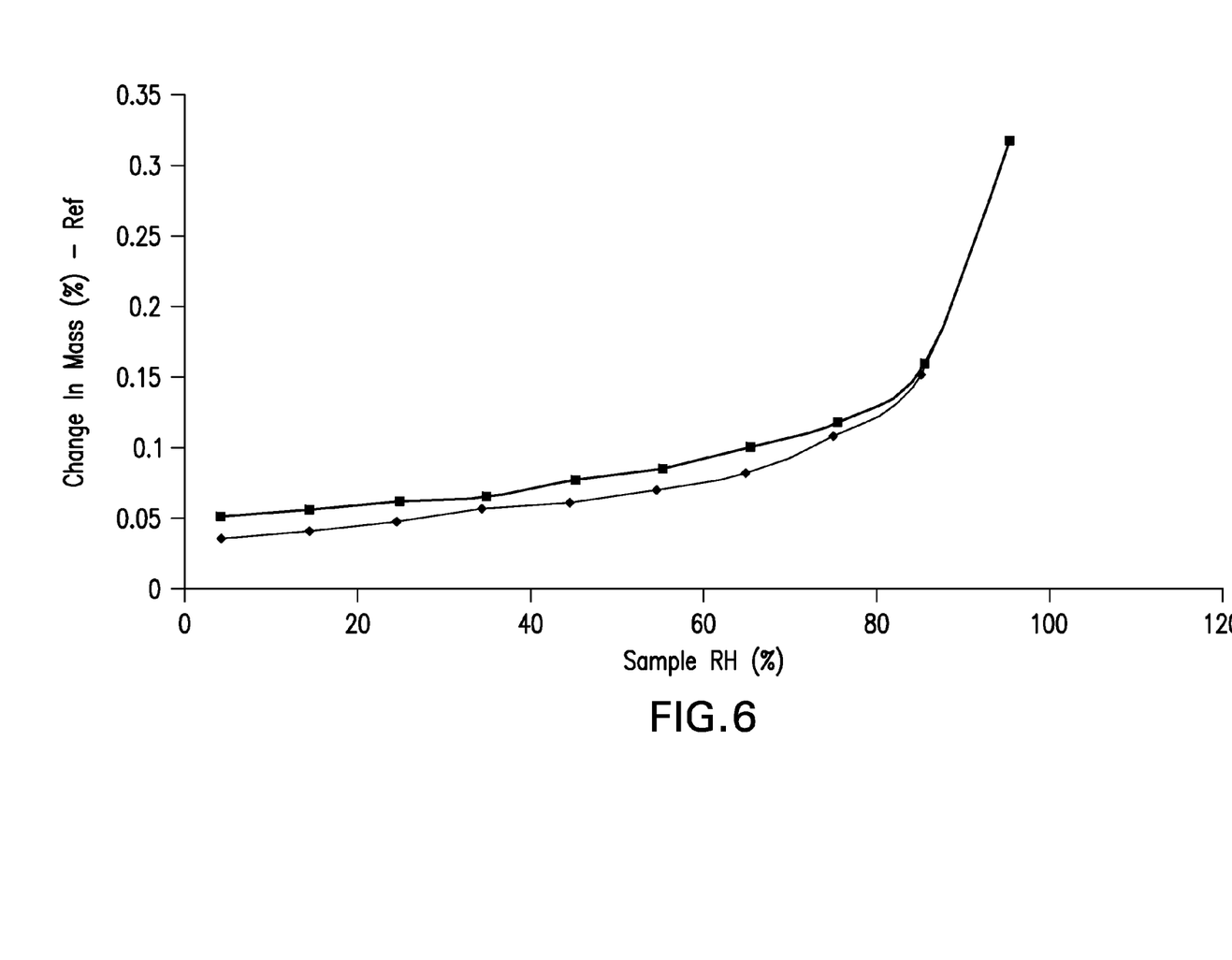
FIG. 6 is a graph a dynamic vapor sorption (DVS) isotherm of the co-crystal of vorapaxar and aspirin having a molar ratio of vorapaxar to aspirin of 1:1 in the unit cell. The graph plots the change in mass (percentage) versus relative humidity (percentage).

FIG. 6 depicts a DVS isotherm plot of the co-crystal of vorapaxar and aspirin (molar ratio 1:1) performed on a DVS Intrinsic dynamic gravimetric sorption analyzer by Surface Measurement Systems Ltd (Alperton, Middlesex, UK). Approximately 10 mg of the co-crystal was placed on the sample pan for analysis. The relative humidity was cycled from 5% to 95% to 5% in 10% increments at 25° C. while measuring the sample mass. The equilibrium criterion (dm/dt) was set to 0.005.

The DVS isotherm indicates that the co-crystal does not absorb a significant amount of water even at high relative humidity.

Electrospray Mass Spectrometry and HPLC-UV

Figure 7:
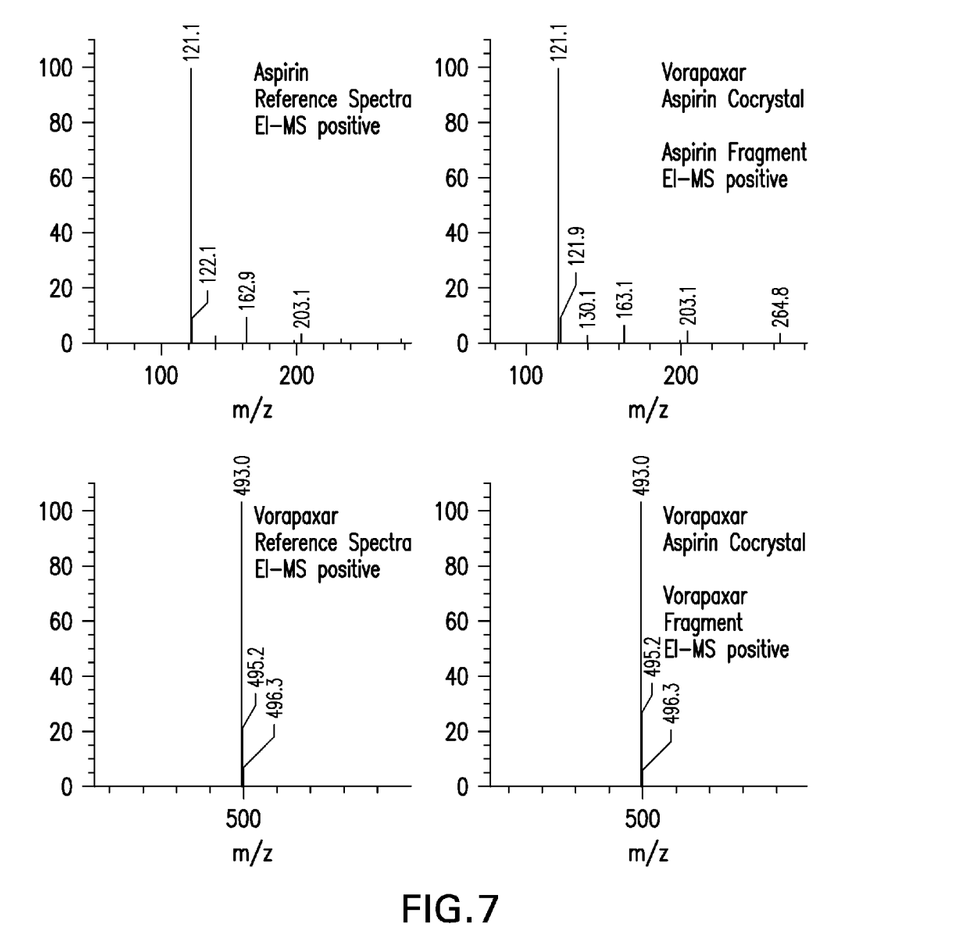
FIG. 7 is a graph comparing the electrospray mass spectrometry (EMS) for vorapaxar, aspirin and the co-crystal of vorapaxar and aspirin having a molar ratio of vorapaxar to aspirin of 1:1 in the unit cell.
Figure 8:
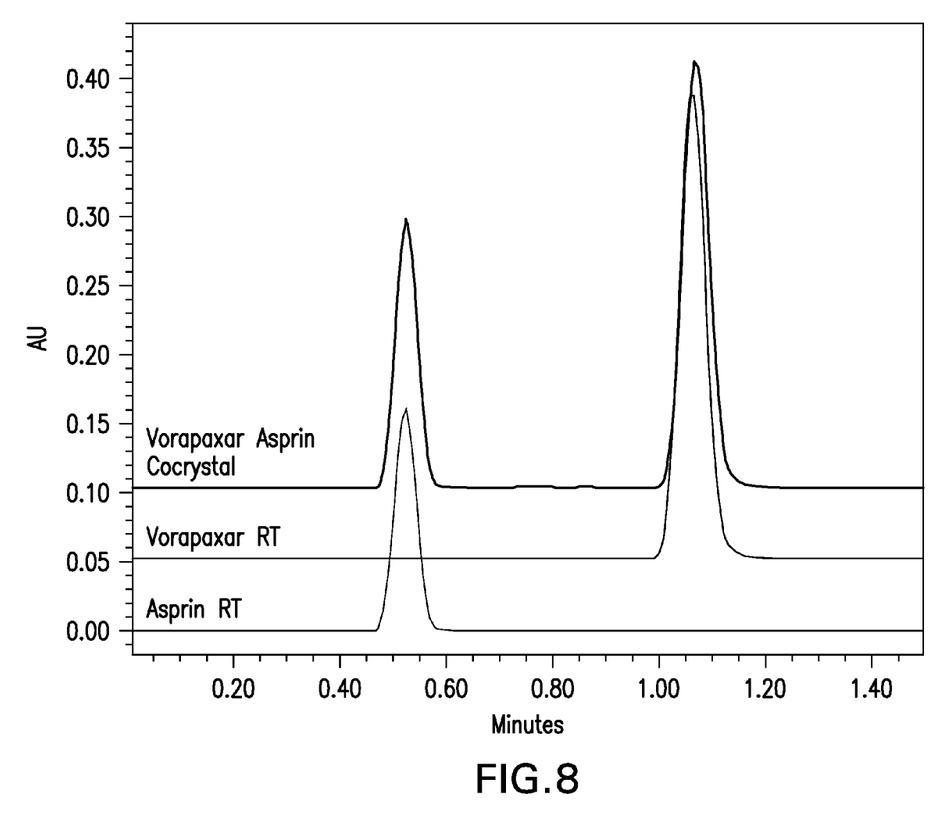
FIG. 8 is a graph comparing the HPLC-UV for vorapaxar, aspirin and the co-crystal of vorapaxar and aspirin having a molar ratio of vorapaxar to aspirin of 1:1 in the unit cell.

FIG. 7 provides EMS data for vorapaxar, aspirin and the co-crystal of vorapaxar and aspirin (molar ratio 1:1) and FIG. 8 is a plot comparing vorapaxar, aspirin and the co-crystal. The data was collected on an Agilent Technologies LCMS, model 11MSD (Santa Clare, Calif., US) with electrospray ionization ("ES") in the positive scan mode. The high-pressure liquid chromatograph was preformed on an Alliance 2695 by Waters Corp. (Milford, Mass. US) fitted with a photo array detector. Calculations were made using a signal observed at 215 nm. "RT" denotes "retention time".

FIG. 7 taken with FIG. 8 confirm that both vorapaxar and aspirin are present in the co-crystal and that the co-crystal is actually a co-crystal of vorapaxar and aspirin and is not a new crystal form of one of the components of the co-crystal or a decomposition product of either vorapaxar or aspirin.

Single-Crystal X-Ray Structure

The single crystal structure of the vorapaxar-aspirin co-crystal was determined. Single crystals were grown by slow evaporation from acetonitrile at 50° C. A single crystal with the approximate dimensions of 0.10 mm×0.50 mm×0.50 mm was mounted on a nylon loop with Paratone-N oil. Data was acquired with a Bruker SMART APEX diffractometer equipped with a graphite monochromated molybdenum Kα source (λ=0.71073). The data were integrated with the Balker SAINT software package (v. 6.0) using a narrow-frame algorithm. Data were corrected for absorption effects using the multi-scan method (SADABS). The structure was solved and refined using the Balker SHELXTL™ Software Package including SHELXS-97.

Figure 9:
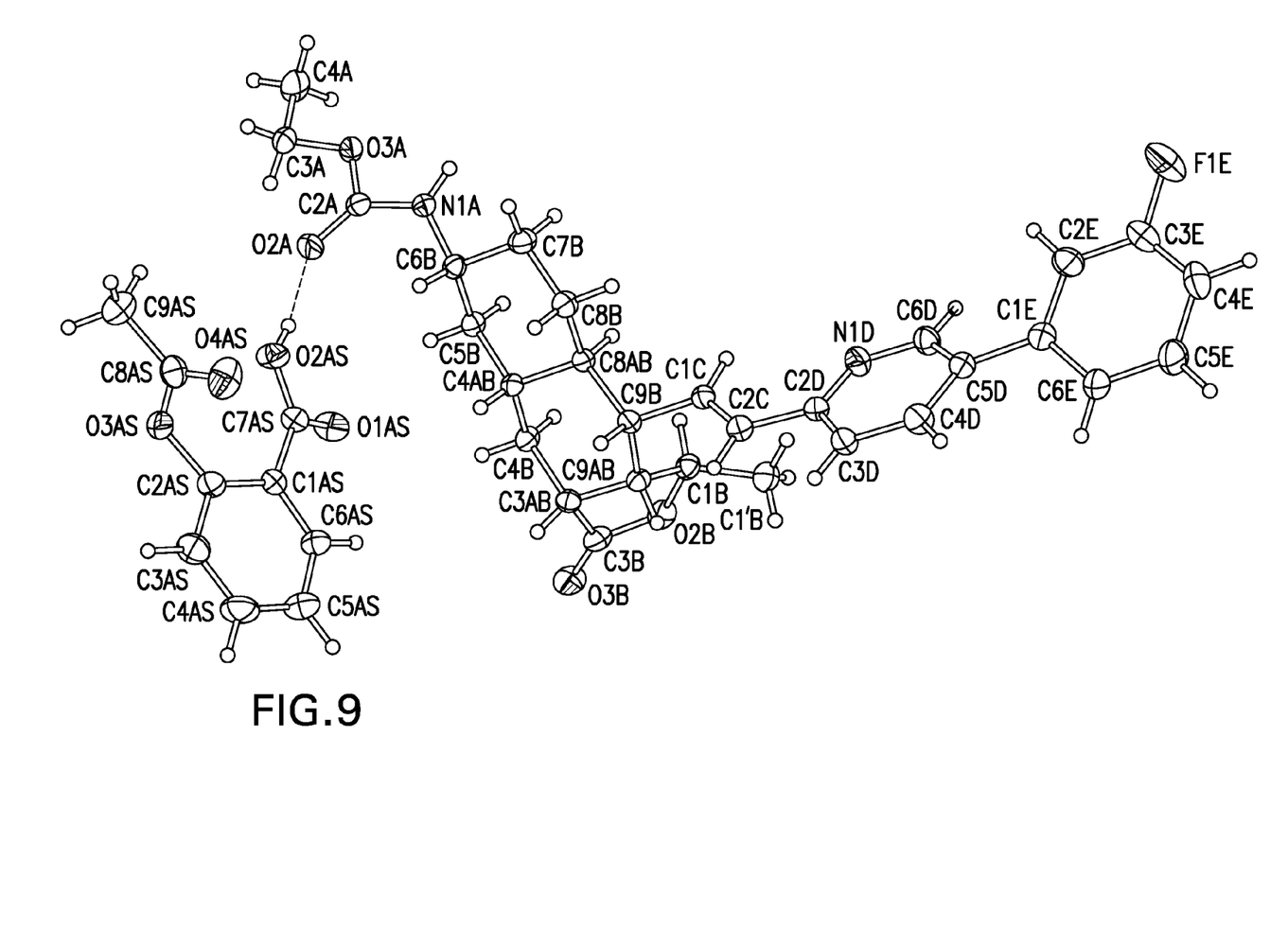
FIG. 9 is an ORTEP drawing of the single crystal structure of the co-crystal of vorapaxar and aspirin having a molar ratio of vorapaxar to aspirin of 1:1 in the unit cell.

The acquisition and cell parameters that were determined for the vorapaxar-aspirin co-crystal are shown in Table 3. FIG. 9 is an ORTEP drawing of a single crystal structure of the vorapaxar-aspirin co-crystal. The ORTEP drawing provides the exact position in space of every atom within the co-crystal and can be used to generate a complete three dimensional image of the co-crystal. These data provide confirmation that the inventive crystalline product is a co-crystal of vorapaxar and aspirin and is not a co-crystal of a decomposition product of either component. The single crystal structure also demonstrates the two molecules interact through hydrogen bonding between the hydrogen atom on the carboxylic acid functional group of aspirin and the oxygen atom of the amide functional group on vorapaxar. This hydrogen bonding arrangement and lack of proton transfer confirm that the complex is a co-crystal and not a salt.

TABLE 3

| Crystal system | orthorhombic | |
|---|---|---|
| Space group | $P\ 2_1\ 2_1\ 2_1$ | |
| Temperature | 296 K | |
| Unit cell dimensions | a = 9.6829(11) Å | α = 90° |
| | b = 12.3767(14) Å | β = 90° |
| | c = 28.470(4) Å | γ = 90° |
| Volume | 3411.9(7) Å$^3$ | |
| Z | 4 | |
| Density (calculated) | 1.310 g/cm$^3$ | |

Dosing and Formulation

The amount and frequency of administration of the inventive co-crystal will be regulated according to the judgment of the attending clinician considering such factors as age, condition and size of the patient as well as the severity of the symptoms being treated.

The daily dose of active compound (i.e., the inventive co-crystal) for the treatment of a disease or condition cited above is about 0.001 for about 100 mg/kg of body weight per day, e.g., from about 1 mg to about 75 mg, from about 1 mg to about 50 mg, (e.g., 2.5 mg) according to the particular application.

The inventive co-crystal may also be useful in combination (administered together or sequentially) with one or more additional therapeutic agents, such as, for example, another cardiovascular agent. Cardiovascular agents that could be used in combination with the co-crystal of the present invention include drugs that have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, MI, glomerulonephritis, thrombotic and thromboembolic stroke, PAD, other cardiovascular diseases, cerebral ischemia, inflammatory disorders and cancer, as well as other disorders in which thrombin and its receptor play a pathological role. Suitable cardiovascular agents include thromboxane A2 biosynthesis inhibitors such as aspirin; thromboxane antagonists such as seratrodast, picotamide and ramatroban; adenosine diphosphate (ADP) inhibitors such as clopidogrel; angiotensin antagonists such as valsartan; telmisartan; candesartan, irbesartan, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists, including salts, esters, and prodrugs of said additional therapeutic agents.

In an embodiment the inventive co-crystal is combined with aspirin.

In another embodiment the inventive co-crystal is combined with clopidogrel.

Other possible combinations may include lipid lowering agents (e.g., simvastatin, lovastatin, pravastatin, atorvastatin rosuvastatin, ezetimibe); niacin in immediate-release or controlled release forms, and particularly in niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone statins, simvastatin, atorvastatin and rosovastatin) and CETP inhibitors, e.g., anacetripib, dalcitrapib, etc.

The dosage of the cardiovascular agent can be determined from published material, and may range from 1 to 1000 mg per dose.

Other therapeutic agents could include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases; conditions; or injuries, radiation fibrosis, endothelial dysfunction, periodontal diseases and wounds. Further examples of therapeutically effective agents which may be administered in combination with the inventive co-crystal include resistance factors for tumor cells towards chemotherapy and proliferation inhibitors of smooth muscle cells, endothelial cells, fibroblasts, kidney cells, osteosarcoma cells, muscle cells, cancer cells and/or glial cells.

For preparing pharmaceutical compositions comprising the inventive co-crystal, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar and lactose. Tablets, powders, sachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations which are intended to be converted, shortly before use, to liquid form preparations for either oral or parenteral administration. Such liquid forms include solutions, suspensions and emulsions.

The co-crystal of the invention may also be deliverable transdermally. The transdermal compositions can take the form of creams, lotions, aerosols and/or emulsions and can be included in a transdermal patch of the matrix or reservoir type as are conventional in the art for this purpose.

Typically, the co-crystal is administered orally, such as, for example, in a unit dosage form. In such form, the preparation is subdivided into suitably sized unit doses containing appropriate quantities of the active component, e.g., an effective amount to achieve the desired purpose.

The following examples are provided so that the invention might be more fully understood. They should neither be construed as forming the only genus that is considered as the invention nor limiting the invention in any way.

Synthesis of the Co-Crystal of Vorapaxar and Aspirin

Scheme 1 shows the reaction scheme to prepare the co-crystal of vorapaxar and aspirin. Vorapaxar was synthesized internally using the procedure published in U.S. Pat. No. 7,605,275. Acetylsalicylic acid (aspirin) and solvents were obtained from commercial sources and used as received without any additional purification. Approximately one molar equivalent of vorapaxar and approximately one molar equivalent of aspirin were stirred in a solvent such as toluene, heptane or a mixture of water with methanol at room temperature. The co-crystal was isolated by filtration or centrifugation followed by decantation of the supernatant.

Scheme 1

Vorapaxar

+

Acetylsalicylic Acid (Aspirin)

1:1 Co-crystal

Example 1

A 100 mL round bottom flask was charged with vorapaxar (2.009 grams, 4.08 millimoles), acetylsalicylic acid (0.739 grams, 4.10 millimoles), and toluene (40 milliliters). The mixture was stirred for 65 hours at room temperature then solids were isolated by filtration. Solids were washed with toluene (10 milliliters) then dried under vacuum at room temperature for 1 day to produce the co-crystal of vorapaxar and acetylsalicylic acid.

Example 2

A mortar was charged with vorapaxar (0.2643 grams, 0.536 millimoles) and acetylsalicylic acid (0.0971 grams, 0.539 millimoles) then ground with a pestle for 5 minutes. Two drops of dimethylacetamide were then added to the mixture and grinding continued for an additional 1 minute to produce the co-crystal of vorapaxar and acetylsalicylic acid.

Example 3

An 8 milliliter vial was charged with vorapaxar (0.1574 grams, 0.320 millimoles), acetylsalicylic acid (0.0582 grams, 0.323 millimoles), and heptane (5 milliliters). The mixture was stirred for 9 days at room temperature then the vial was centrifuged, the supernatant was decanted off of the solids, and the solids were dried under vacuum at room temperature to produce the co-crystal of vorapaxar and acetylsalicylic acid.

Example 4

An 8 milliliter vial was charged with vorapaxar (0.1477 grams, 0.300 millimoles), acetylsalicylic acid (0.0540 grams, 0.300 millimoles), and water (2 milliliters), The mixture was stirred for 1 day at room temperature, then methanol (0.50 milliliters) was added. The mixture was stirred for an additional 8 days at room temperature. The vial was then centrifuged, the supernatant was decanted off of the solids, and the solids were dried under vacuum at room temperature to produce the co-crystal of vorapaxar and acetylsalicylic acid.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A co-crystal of vorapaxar and aspirin.

2. The co-crystal according to claim 1 having a molar ratio of vorapaxar to aspirin of 1:1 in the unit cell.

3. The co-crystal according to claim 2 having characteristic peak locations at degrees 2 theta of 16.9, 18.1, 20.5 and 23.0 measured by X-ray powder diffraction.

4. The co-crystal according to claim 2 having characteristic peak locations at degrees 2 theta of 14.2, 16.9, 18.1, 19.3, 20.5, 23.0, 23.4, and 24.1 measured by X-ray powder diffraction.

5. The co-crystal according to claim 2 having characteristic peak locations at degrees 2 theta of 7.7, 14.2, 16.9, 18.1, 18.9, 19.3, 20.5, 21.9, 23.0, 23.4, 24.1, and 25.0 measured by X-ray powder diffraction.

6. The co-crystal according to claim 1 having the same x-ray diffraction pattern as FIG. 1.

7. The co-crystal according to claim 1 having an endothermic peak at about 148.7° C., measured by differential scanning calorimetry.

8. The co-crystal according to claim 1 having an endothermic peak at about 148.7° C., measured by differential scanning calorimetry and having characteristic peak locations at degrees 2 theta of 14.2, 16.9, 18.1, 19.3, 20.5, 23.0, 23.4, and 24.1, measured by X-ray powder diffraction.

9. A pharmaceutical composition comprising the co-crystal according to claim 1 and a pharmaceutically acceptable carrier.

10. The pharmaceutical composition according to claim 9 which comprises a second therapeutic agent.

11. The pharmaceutical composition according to claim 10, wherein the second therapeutic agent is aspirin.

12. A method for treating acute coronary syndrome, secondary prevention peripheral arterial disease, thrombosis, atherosclerosis, restenosis, hypertension, angina pectoris, arrhythmia, heat failure, myocardial infarction, glomerulonephritis, thrombotic stroke, thromboembolic stroke, deep vein thrombosis, venous embolism a cardiovascular disease associated with hormone replacement therapy, renal ischemia, cerebral stroke, cerebral ischemia, cerebral infarction, migraine, or renal vascular homeostasis in a mammal in need thereof which comprises administering to said mammal an effective amount of a co-crystal according to claim 1.

13. A method of inhibiting platelet aggregation in a mammal in need thereof which comprises administering to said mammal an effective amount of the co-crystal of vorapaxar and aspirin.

* * * * *

UNITED STATES PATENT AND TRADEMARK OFFICE
CERTIFICATE OF CORRECTION

PATENT NO. : 9,604,971 B2
APPLICATION NO. : 14/905193
DATED : March 28, 2017
INVENTOR(S) : Trzaska et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 31 days.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*